Figure 1:
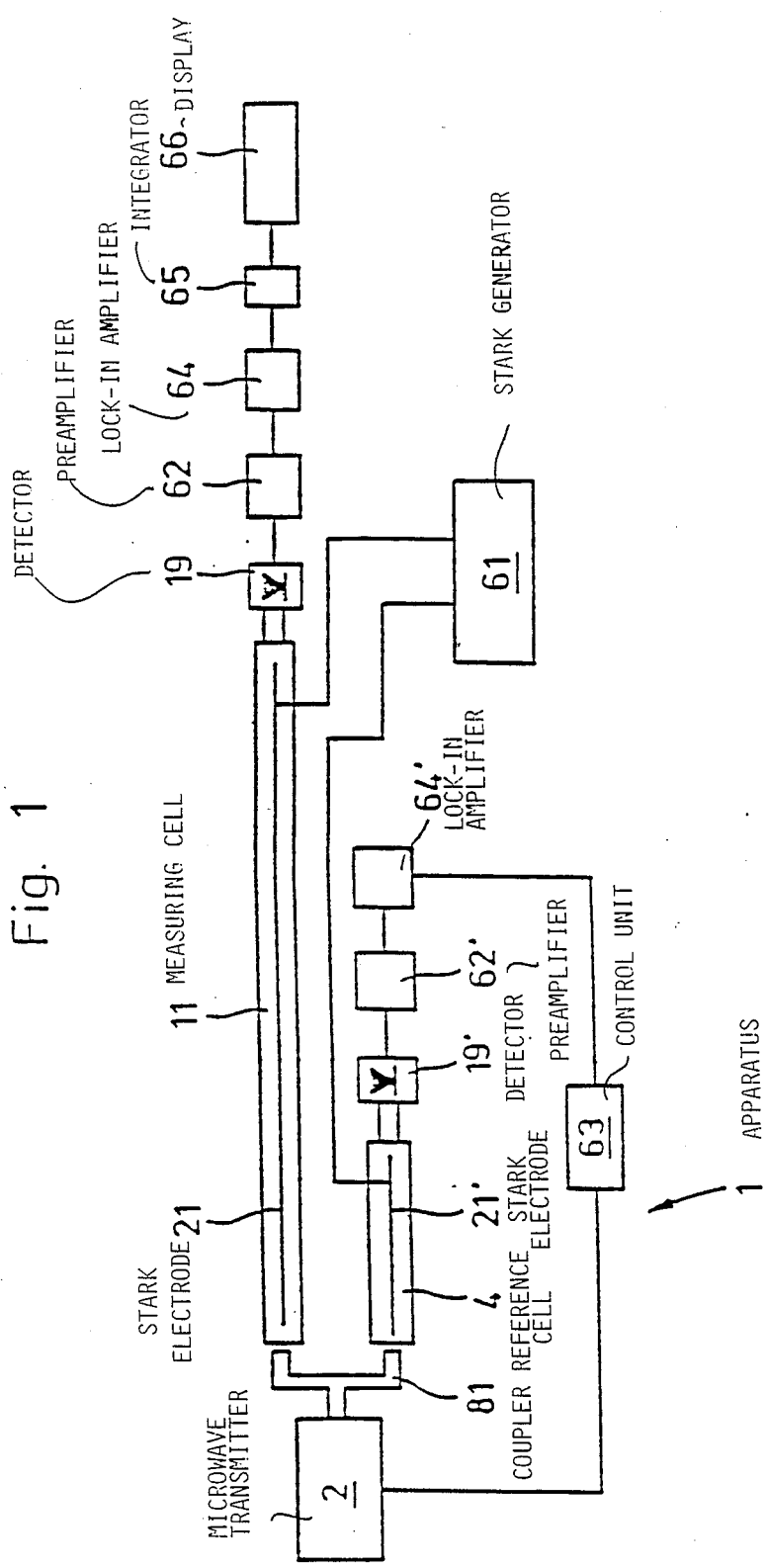

United States Patent [19]

Berger et al.

[11] Patent Number: 4,972,699
[45] Date of Patent: Nov. 27, 1990

[54] METHOD AND APPARATUS FOR ANALYSIS BY MEANS OF MICROWAVES

[75] Inventors: Lutz Berger, Eggenstein-Leopoldshafen; Gunther Krieg; Gerhard Schmitt, both of Karlsruhe, all of Fed. Rep. of Germany

[73] Assignee: Kernforschungszentrum Karlsruhe GmbH, Karlsruhe, Fed. Rep. of Germany

[21] Appl. No.: 327,808

[22] PCT Filed: Jul. 8, 1988

[86] PCT No.: PCT/DE88/00431
§ 371 Date: Mar. 17, 1989
§ 102(e) Date: Mar. 17, 1989

[87] PCT Pub. No.: WO89/00684
PCT Pub. Date: Jan. 26, 1989

[30] Foreign Application Priority Data
Jul. 17, 1987 [DE] Fed. Rep. of Germany ....... 3723606

[51] Int. Cl.[5] ............................................. G01N 22/00
[52] U.S. Cl. ..................................... 73/23.2; 324/639
[58] Field of Search .............. 73/23; 324/58.5 C, 639

[56] References Cited

U.S. PATENT DOCUMENTS 3,973,186  8/1976  Uehara et al. ............... 324/300 X
4,607,521  8/1986  Saito et al. ..................... 73/23

OTHER PUBLICATIONS

Archiv für Elektronik und Ubertragungstechnik; vol. 40, No. 5i pp. 313-320.
Instruments and Experimental Techniques; vol. 17, No. 3, Part II, pp. 777-778.

Primary Examiner—Hezron E. Williams
Assistant Examiner—Joseph W. Roskos
Attorney, Agent, or Firm—Spencer & Frank

[57] ABSTRACT

A method for analyzing a gas by means of microwave absorption including the steps of: generating a microwave at at least one frequency; continuously sweeping the microwave frequency over the absorption frequency of a known pure gas component; transmitting the microwave frequency to a measuring cell containing the gas to be measured and to a reference cell containing the known pure gas component; detecting an absorption measurement signal from the measuring cell; detecting an absorption reference signal from the reference cell; integrating the intensity of the measurement signal; and applying an alternating Stark voltage with a phase shift to the measuring cell and to the reference cell. Also provided is an apparatus which may be used in conjunction with this method.

14 Claims, 2 Drawing Sheets

METHOD AND APPARATUS FOR ANALYSIS BY MEANS OF MICROWAVES

The invention relates to a method of analyzing gaseous media by means of microwave absorption, particularly for the determination of gas concentrations, wherein a microwave is generated at at least one frequency. The invention also relates to an apparatus for analyzing gaseous media by means of the absorption of microwaves, particularly for a determination of concentrations, primarily for implementing the method and comprising at least one microwave transmitter, at least one measuring cell, at least one detector, amplifying and display devices for the measurement signal as well as a control device for the microwave transmitter.

It is known to analyze gaseous media, possibly also after conversion of a solid or a liquid into the gaseous state, by absorption of microwaves within certain characteristic frequency ranges by the excitation of rotational transitions in molecules of the media to be examined. In order to reduce the line width, the examination takes place in the low pressure range. The absorption lines are split by means of the Stark effect, with an alternating Stark voltage preferably being applied to increase detection sensitivity. Such a process is highly selective, in principle, but does not require prior modifications, such as ionization or chemical reactions, of the substances to be examined.

In the past, this examination method could be used practically only in a laboratory setting. Industrially usable devices were not available since the known devices were expensive because of their structural, mechanical as well as electrical configuration, sometimes included sensitive components and it was difficult or expensive to stay within critical parameters.

For example, it is necessary to stabilize and thus regulate (in its actual sense) the frequency of the transmitted microwave with respect to the absorption maximum of the molecule of interest, possibly under consideration of the Stark voltage that is acting on it. For this purpose, it has been proposed to feed part of the high frequency of the microwave radiation, with the aid of directional coupler, to a mixer diode, to there compare it with the harmonic of a stable low frequency transmitter generated, for example, by a quartz crystal, to bind it to the harmonic of the low frequency by synchronization by means of a PLL [phase locked loop] circuit and thus stabilize the high frequency of the microwave on the absorption line of the component to be measured. It has also been proposed to additionally modulate the microwave transmitter, to send part of the microwave radiation through a reference cell containing the component to be measured, with the splitting of the microwave radiation again requiring the use of a directional coupler. With the aid of the derivation signal at the detector of the reference cell, which is required in addition to the detector at the measuring cell, the microwave transmitter is fixed on the absorption line of the component to be measured.

The drawback of transmitter modulation becomes evident on the basis of the increased noise power in the detector as a result of it. The prior art microwave methods and devices were too expensive, particularly because of the complicated frequency stabilization, so that competing different types of measuring methods and devices were more economical.

It is the object of the invention to provide a method of this type which provides an economical analysis of gaseous media, particularly a determination of their concentration while avoiding the stated drawbacks and which provides prerequisites for an industrially usable microwave analyzer.

According to the invention this stated object is attained by a method of the above-mentioned type which is characterized in that the microwave frequency is continuously swept over the absorption frequency of an anticipated gas and the intensity of the absorption is integrated. A device according to the invention has such a configuration that the microwave frequency is continuously swept over the absorption frequency of an anticipated gas and the intensity of the absorption is integrated. In a preferred embodiment it is provided that the frequency range for sampling and integration are [sic] determined by the reference signal of a known pure gas component. A further feature provides that, if the absorption line is split by means of a Stark effect, an alternating Stark voltage is applied in which case the alternating Stark voltage is applied with a phase shift to the gas to be measured, on the one hand, and to the pure gas component, on the other hand, and, in particular, the alternating Stark voltage is applied with a phase shift of 90 degrees. In this way it is possible, if required, to provide only one preamplifier for the reference signal as well as the measurement signal, with, in particular, the preamplification being effected by means of a subcritically attenuated narrowband passive network. It may further be provided that the high Stark voltage is supplemented by an inductance which directly supplements the Stark capacitance to form a parallel resonant circuit and constitutes the high voltage coil of a transformer.

A preferred embodiment of the device according to the invention provides that the control device for continuously controlling a frequency determining voltage for the microwave transmitter is configured by way of an adjustable frequency range and the detector has an associated integrator for integrating the measurement signals during the change of the microwave frequency. In order to control the sampling by means of a reference cell, it is provided that the measuring cell has at least one reference cell arranged in parallel with it whose detector is connected with the control device for the microwave transmitter, with, in particular, at least one Stark generator being provided which feeds a modulated Stark signal to the measuring cell and possibly to the reference cell.

If several absorption frequencies are to be examined, it may be provided that a plurality of microwave transmitters covering different frequency ranges are associated with one measuring cell. In this case, in order to avoid the exchange of the pure gas generator, for example a permeation system in the reference cell, a modification of the invention may provide that a plurality of reference cells are associated with one measuring cell, with the reference cells being connected mutually in parallel or in series. In any case, the reference cells as a whole are arranged in parallel with the measuring cell. In such multi-component systems, the microwave transmitters, which preferably include Gunn oscillators, are connected by means of a coupler with the measuring cell, on the one hand, and with the reference cell or cells, on the other hand. If a plurality of reference cells are employed, suitable waveguide switches may be provided for switching between the reference cells.

Another significant feature of such an embodiment is that otherwise the entire arrangement, particularly the electronic evaluation system, remains the same. The various components are measured by actuation of the respective transmitter and applying the respective Stark voltages. This may, however, involve switching delays. Therefore, it is preferred to provide two transmitters, particularly if two components are to be measured, with these transmitters being connected to the measuring cell by way of switches.

The configuration according to the invention has the particular advantage that only one Stark generator need be employed. Moreover, because of the parallel arrangement of measuring cells and reference cells, lower-power microwave transmitters can be employed which are less expensive than high-power transmitters. Additionally, it is not absolutely necessary to provide for thermostatic control of the reference cell since it operates with the rotational transitions completely modulated out.

Figure 2:
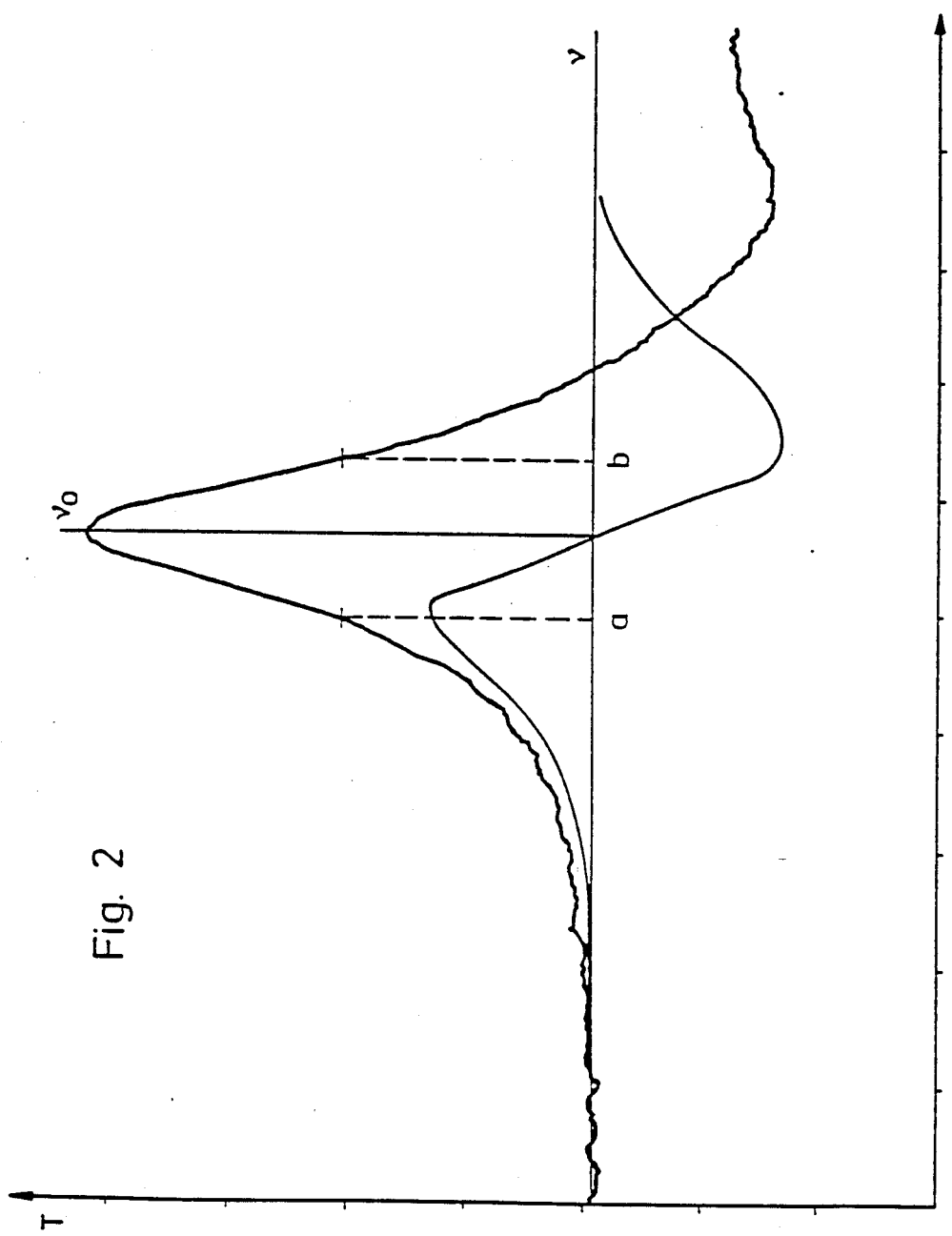

Further advantages and features of the invention will become evident from the claims and from the subsequent description in which one embodiment will be described with reference to the drawing. It is shown in:

FIG. 1, a schematic representation of the apparatus according to the invention; and FIG. 2, a diagram of an absorption line.

The apparatus 1 according to the invention includes a microwave transmitter 2, followed by the parallel connection, via a coupler 81, of a reference cell 4 and a measuring cell 11. Measuring cell 11 has an associated detector 19 and the reference cell has an associated detector 19'. Additionally, measuring cell 11 and reference cell 4 include Stark electrodes 21, 21' which are connected with a common Stark generator 61. The Stark field in the reference cell is at least as large as that in the measuring cell.

The mechanical structure of the apparatus may correspond in its components to that disclosed in [German] Patent Application P 3,622,956.3 corresponding to U.S. application Ser. No. 07/071,655 filed Jul. 9th, 1987 now U.S. Pat. No. 4,896,097 issued Jan. 23rd, 1990, with measuring cell 11 and reference cell 4 arranged in parallel by way of coupler 81.

In particular, measuring cell 11, but also reference cell 4, may be arranged, if necessary, in the shape of a meander in order to avoid unduly long structural lengths and may each be subdivided into several 180 degree arcs and linear Stark chamber regions. The cross sections of the measuring cell and of the reference cell are optimized for the respective microwave range in which the device is intended to operate and, in particular, if only on frequency is to be analyzed, tuned to that frequency. Preferably the microwave transmitter includes a Gunn oscillator.

If several gas components are to be analyzed, several transmitters can be connected to associated measuring and reference cells, in each case by way of appropriate waveguide switches. The Stark voltages in the measuring cell and in the reference cell are each added to correspond to the transmitters. In a multi-component system it may also be provided that, if the respective component for the reference cell is made available in pure form, several reference cells are arranged downstream of the respectively associated transmitters, in parallel with one another or all of them in series but in any case all of them together in parallel with the measuring cell which are then switched in corresponding to the respective measurement to be made.

The required Stark capacitance is formed in a cell 4, 11 and an electrode 21, 21' held insulated therein or by a septum. The Stark voltage supply is configured in such a manner that it includes an external inductance which broadens the capacitance of the internal Stark electrode to form a parallel resonant circuit and this inductance may simultaneously constitute the high voltage coil of a transformer.

Reference cell and measuring cell are temperature controlled and can be held at the same temperature. A constant pressure must be maintained particularly in the reference cell. For this purpose, a conventional vacuum pump is connected to the outlet of the reference cell. The outlet includes a capillary by means of which a constant gas flow is realized. If only one vacuum system is employed, a filter is connected downstream of the capillary so as to absorb the component to be measured and thus prevent it from reaching the measuring cell as a pure substance which would falsify the measurement. The pure substance required for reference cell 4 is made available by a permeation vessel containing it. This vessel is provided with a separate heating and/or cooling system. This system is controlled in the following manner by a pressure regulator connected with a pressure sensor. If the suction power of a vacuum system varies, pressure fluctuations may occur in spite of the capillary. These pressure fluctuations are measured by the pressure sensor which, by way of pressure regulation, either heats the permeation vessel—if the pressure drops so as to realize increased permeation of the pure component—or reduces heating output or cools—if the pressure rises to thus reduce the permeation output. This results in an accurate and reliable pressure regulation, with the pressure in the reference cell corresponding to at least the pressure in the measuring cell.

If it should be necessary, for a particular application, to integrate over the entire line in the measuring cell, the pressure in the reference cell is selected to be higher than the pressure in the measuring cell. This generally also requires a greater Stark field in the reference cell to ensure complete out-modulation of the absorption line there. To prevent crosstalk between the relatively strong signals detected in the reference branch and the measuring branch, the phase shift between the alternating Stark voltage in the reference cell and the alternating Stark voltage in the measuring cell is 90 degress.

In the illustrated embodiment, detectors 19, 19' are each connected with their own preamplifier 62, 62'. Measuring and reference branch each have their own preamplifiers 62 and 62', respectively, and their own lock-in amplifiers 64 and 64', respectively. An integrator 65 downstream of the lock-in amplifier or measuring branch 64 furnishes a value which corresponds to the concentration of the gas being measured and is indicated at 66.

In principle, they may also be connected to a common preamplifier. The latter would require that the Stark generator 61 furnish phase shifted Stark voltages—preferably voltages shifted by 90 degrees—to the two cells 4, 11 so that the two measuring results from detectors 19, 19' can be processed in succession by the common preamplifier. Preamplifiers 62, 62' are then followed, on the one hand, by a lock-in amplifier 64' which receives the voltage of reference cell detector 19, to regulate microwave transmitter 2 by way of control unit 63 and, on the other hand, a lock-in amplifier 64 including an integrator, an integrator 65 as well as, following thereafter, a display 66.

The reference branch performs two tasks:

1. Finding the absorption line.

Reference cell 4 includes the component to be measured in pure form. When the device is switched on, the Gunn element oscillates at some frequency within a narrowband tuning range (about 50 MHz). A voltage ramp furnished by electronic unit 63 tunes the transmitter over the tuning range. At the absorption frequency $\omega_0$ of the component to be measured, lock-in amplifier 64 of the reference branch, if it is tuned to $U_0$, furnishes a signal maximum to electronic control system 63. During measuring operation, the tuning voltage is varied around this value $U_0$ by a value $\pm \Delta U$.

2. Fixing the integration limits:

As disclosed in the present patent, electronic unit 63 in measuring operation takes care that the tuning voltage of the transmiter is varied between the values $U_0-\Delta U$ (corresponds to point a on the frequency scale in FIG. 2) and $U_0+\Delta U$ (corresponds to point b on the frequency scale in FIG. 2). Between these two voltage and frequency values, respectively, the signals of the lock-in amplifier of the measuring branch are integrated 65 and are displayed 66.

In the method according to the invention, the electronic system 63 now continuously sweeps the frequency of microwave high frequency transmitter 2 over the absorption line $v_0$-for example 28.97 GHz for a Stark field intensity of E=800 V/cm for formaldehyde. The microwave is divided by way of coupler 81. Both cells 11, 4 operate at the same Stark voltage which causes the rotational transitions to be modulated but, as already mentioned, at a phase difference of 90 degrees. The regulation may start, for example, at a. As can be seen in FIG. 2, this regulation results in an ascending voltage ramp; as soon as absorption line $v_0$ has been exceeded, which is caused by the reference signal (shown in FIG. 2) produced by the pure gas in reference cell 4, for example in that a given voltage value at a frequency b is not attained, the control voltage across the high frequency transmitter is reduced and thus the absorption line is sampled again. When it is exceeded again, the control system on the other side of the line switches again and increases the voltage applied to the oscillator. Between the voltage reversal points, the signal present at detector 19 of measuring cell 11 is integrated by integrator 65. The integration value is a measure of the concentration of the gas in measuring cell 11. The response time of the process is fixed by the time required to scan the line and lies in an order of magnitude of 30 to 60 seconds which, however, is sufficient in many cases.

The amplifiers are phase selective. Measurement and reference signals shifted by 90 degrees relative to one another can be separated by suitable phase positions of the sampling times in the measuring and reference branches of th circuit. This is done in that for the signal picked up by the detector and including reference and measurment components, only that component which is in phase with the control voltage is rectified in each branch so that the 90 degrees phase shifted component becomes evident.

Phase shifts in the measurement and reference signals reaching the lock-in amplifier from the detector relative to the alternating Stark voltages caused by electronic components can be considered by means of a digital phase shifter. For this purpose, an oscillator signal from which, for example, the frequency of the Stark voltage has been derived by division, is fed to a counter which is set to its preselected binary value by a set signal, for example the signal on which the alternating Stark voltage is based. At a time corresponding to the binary value after setting, output pulses appear which are converted in a known manner into a symmetrical wave at the frequency of the set signal now shifted by the desired phase shift. This wave then constitutes the above-mentioned control signal.

With a quartz oscillator output frequency of, for example, 10 MHz and fixed division by 200 it is possible, for example, to effect a phase shift in 200 steps of 1.8 degrees each. The phase shift can be switched on once and can be automatically reproduced when the device is switched on again. It may be actuated directly by a computer. A frequency determining bias is obtained from the reference signal of the reference cell and is fed to the oscillator. If, due to the fact that the microwave frequency runs out of the absorption frequency and thus a finite voltage is produced in the reference branch from the zero passage of the reference signal, control system 63 provides a corresponding correction voltage.

The measurement signal may be displayed or further used for process control.

We claim:

1. Method of analyzing a gas by means of microwave absorption comprising the steps of:
   generating a microwave at at least one frequency;
   continuously sweeping the microwave frequency over an absorption frequency of a known pure gas component;
   transmitting the microwave frequency to a measuring cell containing the gas to be measured and to a reference cell containing the known pure gas component;
   detecting an absorption measurement signal from the measuring cell;
   detecting an absorption reference signal from the reference cell;
   integrating the intensity of the measurement signal; and
   applying an alternating Stark voltage having a phase shift to the measuring cell and to the reference cell.

2. Method according to claim 1, wherein the frequency range for sampling and integration is determined by the reference signal.

3. Method according to claim 1, characterized in that the alternating Stark voltage is applied with a phase shift of 90 degrees in the reference cell and in the measuring cell.

4. Method according to claim 1, wherein the Stark voltage is supplemented by an inductance which directly supplements a Stark capacitance to form a parallel resonant circuit and comprises a high voltage winding of a transformer.

5. Method according to claim 1, wherein the reference and measurement signals are detected by a common detector.

6. Method according to claim 5, wherein at least one of said reference and measurement signals is pre-amplified by a subcritically attenuated, passive LC highpass filter network having a bandpass characteristic at the resonant frequency being utilized.

7. Method according to claim 1, wherein a phase and frequency selective amplification is performed by lock-in amplification.

8. Method according to claim 1, wherein gas is extracted from the reference cell to produce a subatmospheric pressure and wherein the temperature of a permeation system for the pure gas component is regulated in such a manner that the pressure in the reference cell remains constant.

9. Apparatus for the analysis of gaseous media by means of the absorption of microwaves comprising
   at least one microwave transmitter;
   at least one measuring cell;
   at least one detector for detecting absorption by a gas sample placed in the measuring cell and for producing a measurement signal;
   an amplifying means for amplifying the measurement signal;
   a display means for displaying the measurement signal;
   a control device for the microwave transmitter, the control device being configured to continuously control a frequency determining voltage for the microwave transmitter over an adjustable frequency range;
   and an integrator for integration of the measurement signal during the change in the microwave frequency, said integrator being disposed downstream of the detector.

10. Apparatus according to claim 9, wherein at least one reference cell is connected in parallel with the at least one measuring cell and a detector for detecting absorption of the reference cell is connected with the control device (63) for the microwave transmitter (2).

11. Apparatus according to claim 9, further comprising at least one Stark generator which feeds an amplitude modulated Stark signal to the measuring cell and the reference cell.

12. Apparatus according to claim 11, further comprising a phase shifter for producing a phase difference between the Stark voltage for the measuring cell and the Stark voltage for the reference cell (4).

13. Apparatus according to claim 12, further comprising electronic systems associated with the detectors for the measuring and reference cells and located downstream thereof, said electronic systems being tuned to the phase of the Stark signal fed to the reference cell and to the phase of the Stark signal fed to the measuring cell.

14. Apparatus according to claim 9, wherein the microwave transmitter includes a Gunn oscillator.

* * * * *